US010556938B2

(12) United States Patent
Pilon et al.

(10) Patent No.: US 10,556,938 B2
(45) Date of Patent: Feb. 11, 2020

(54) COMPOSITIONS AND METHODS OF USE FOR RECOMBINANT HUMAN SECRETOGLOBINS

(71) Applicant: Therabron Therapeutics, Inc., Rockville, MD (US)

(72) Inventors: Aprile L. Pilon, Rockville, MD (US); Melissa E. Winn, Rockville, MD (US); John K. Zehmer, Rockville, MD (US)

(73) Assignee: APC Research Assets, LLC, Rockville, MD (US)

( * ) Notice: Subject to any disclaimer, the term of this patent is extended or adjusted under 35 U.S.C. 154(b) by 0 days.

(21) Appl. No.: 15/707,934

(22) Filed: Sep. 18, 2017

(65) Prior Publication Data

US 2018/0244735 A1 Aug. 30, 2018

Related U.S. Application Data

(60) Continuation of application No. 14/880,908, filed on Oct. 12, 2015, now Pat. No. 9,765,127, which is a division of application No. 13/843,289, filed on Mar. 15, 2013, now abandoned.

(51) Int. Cl.
    *C12P 21/06* (2006.01)
    *A61K 38/00* (2006.01)
    *C07K 14/47* (2006.01)

(52) U.S. Cl.
    CPC .............. *C07K 14/47* (2013.01); *C12P 21/06* (2013.01); *A61K 38/00* (2013.01)

(58) Field of Classification Search
    None
    See application file for complete search history.

(56) References Cited

U.S. PATENT DOCUMENTS

| | | | |
|---|---|---|---|
| 6,953,666 | B1 | 10/2005 | Kinkade |
| 7,846,899 | B2 | 12/2010 | Pilon |
| 2001/0029025 | A1 | 10/2001 | Dreyfuss |
| 2003/0008816 | A1 | 1/2003 | Pilon |
| 2004/0047857 | A1 | 3/2004 | Pilon |
| 2006/0275794 | A1 | 12/2006 | Carrino |
| 2007/0037246 | A1 | 2/2007 | Butt |
| 2008/0063626 | A1 | 3/2008 | Ding |
| 2009/0004684 | A1 | 1/2009 | Maier |
| 2009/0197808 | A1 | 8/2009 | Pilon |
| 2011/0183887 | A1 | 7/2011 | Pilon |
| 2012/0202740 | A1 | 8/2012 | Kimura |

FOREIGN PATENT DOCUMENTS

| | | | |
|---|---|---|---|
| JP | 200759191 | A | 10/2007 |
| WO | 2004101824 | A1 | 11/2004 |
| WO | WO 2008/039941 | A2 * | 4/2008 |
| WO | 2011047065 | A1 | 4/2011 |

OTHER PUBLICATIONS

International Search Report in PCT/US2014/030117 dated Sep. 29, 2014.
International Preliminary Report on Patentability in PCT/US2014/030117 dated Mar. 2, 2015.
Levine, "Pharmacokinetics, and Anti-inflammatory Effects of Intratracheal Recombinant Human Clara Cell Protein in Premature Infants with Respiratory Distress Syndrome." Pediatric Research 58(1): 15-21 (Jul. 1, 2005).
Cai, "Preclinical evaluation of human secretoglobin 3A2 in mouse models of lung development and fibrosis." American Journal of Physiology—Lung Cellular and Molecular Physiology 306(1):10-22 (Jan. 1, 2014).
Ghanta, "An update on pharmacologic approaches to bronchopulmonary dysplasia." Seminars in Perinatology 37(2):115-123 (Apr. 1, 2013).
Niimi, "UGRP1, a uteroglobin/Clara cell secretory protein-related protein, is a novel lung-enriched downstream target Gene for the T/EBP/NKX2.1 homeodomain transcription factor." Molecular Endocrinology 15(11):2021-36 (Nov. 1, 2001).
Database UniProt (Online) "RecName:Full=Secretoglobin family 3A member 2; AltName:Full=Pneumo secretory protein 1; Short=PnSP-1; AltName:Full=Uterolglobin-related protein 1; Flags: precursor" Retrieved from EBI accession No. UniProt:Q96PL1 Databse accession No. Q96PL1 (Jan. 23, 2002).
Bin, "Identification of uteroglobin-related protein 1 and marophage scavenger receptor with collagenous struture, as a lung-specific ligand-receptor paid." The Journal of Immunology 171(2):924-930 (Jul. 15, 2003).
Antico, "Recombinant human uteroglobin/CC10 inhibits the adhesion and migration of primary human endothelial cells via specific and saturable binding to fibronectin." Journal of Cellular Physiology 207(2):553-561 (May 1, 2006).
Arias-Martinez, "Clara cell protein expression in human neonates during respiratory distress syndrome." Cellular Physiology and Biochemistry 29(5-6): 753-760 (Epub May 11, 2012).
Barnes, "Structural basis for calcium binding by uteroglobins." Journal of Molecular Biology 256(2): 392-404 (Feb. 23, 1996).
Berlett, "Protein oxidation in aging, disease, and oxidative stress." Journal of Biological Chemistry 272(33): 20313-20316 (Aug. 15, 1997).
Cai, "Protein Oxidative Modifications: Beneficial Roles in Disease and Health." Journal of Biochemical and Pharmacological Research 1(1):15-26 (Mar. 1, 2013).
Callebaut, "The uteroglobin fold." Annals of the NY Academy of Sciences 923: 90-112 (Jan. 1, 2000).

(Continued)

*Primary Examiner* — Elizabeth C. Kemmerer
(74) *Attorney, Agent, or Firm* — Henry J. Cittone; Cittone Demers & Arneri LLP

(57) ABSTRACT

Methods of synthetically producing, formulating and using secretoglobins SCGB1A1, SCGB3A2, and SCGB3A1 are provided. Methods of using secretoglobins SCGB1A1, SCGB3A2, and SCGB3A1 as therapeutic agents to affect long term patient outcomes, such as preventing severe respiratory exacerbations of underlying conditions that require medical intervention, including hospitalization are provided. Methods of producing recombinant human secretoglobins, analytical methods, pharmaceutical compositions, and methods of use to prevent the long term sequelae of acute and chronic respiratory conditions are provided.

5 Claims, 6 Drawing Sheets

Specification includes a Sequence Listing.

(56) References Cited

OTHER PUBLICATIONS

Chalker, "Conversion of cysteine into dehydroalanine enables access to synthetic histones bearing diverse post-translational modifications." Angewandte Chemie Int Ed Engl 51(8):1835-1839 (Feb. 20, 2012).
Davies, "Protein damage and degradation by oxygen radicals. II. Modification of amino acids." Journal of Biological chemistry 262(20): 9902-9907 (Jul. 15, 1987).
Folk, "Mechanism of action of guinea pig liver transglutaminase. VI Order of substrate addition." Journal of Biological Chemistry 243(2): 418-427 (Jan. 25, 1968).
Guptasarma, "Hydroxyl radical mediated damage to proteins, with special reference to the crystallins." Biochemistry 31(17): 4296-4303 (May 5, 1992).
Hard, "Solution structure of a mammalian PCB-binding protein in complex with a PCB." Nature Structural Biology 2(11): 983-989 (Nov. 1, 1995).
Hawkins, "Hypochlorite-induced oxidation of amino acids, peptides and proteins." Amino Acids 25(3-4): 259-274 (Jan. 1, 2003).
Hazen, "p-Hydroxyphenylacetaldehyde is the major product of L-tyrosine oxidation by activated human phagocytes. A chloride-dependent mechanism for the conversion of free amino acids into reactive aldehydes by myeloperoxidase." Journal of Biological Chemistry 271(4):1861-1867 (Jan. 26, 1996).
Henderson, "Production of brominating intermediates by myeloperoxidase. A transhalogenation pathway for generating mutagenic nucleobases during inflammation." Journal of Biological Chemistry 276(11): 7867-7875 (Mar. 16, 2001).
Jeon, "Role of protein modifications mediated by transglutaminase 2 in human viral diseases." Frontiers in Bioscience 11: 221-231 (Jan. 1, 2006).
Klug, "Uteroglobin/Clara cell 10-kDa family of proteins: nomenclature committee report." Annals of NY Academy of Sciences 923: 348-354 (Jan. 1, 2000).
Lesort, "Tissue transglutaminase: a possible role in neurodegenerative diseases." Progress in Neurobiology 61(5): 439-463 (Aug. 1, 2000).
Lindahl, "Nasal lavage fluid and proteomics as means to identify the effects of the irritating epoxy chemical dimethylbenzylamine." Biomarkers 9(1): 56-70 (Jan. 1, 2004).
Lindahl, "Demonstration of different forms of the anti-inflammatory proteins lipocortin-1 and Clara cell protein-16 in human nasal and bronchoalveolar lavage fluids." Electrophoresis 20(4-5): 881-890 (Apr. 1, 1999).
Lorand, "Transglutaminases: crosslinking enzymes with pleiotropic functions." Nature Reviews. Molecular Cell . Biology 4(2): 140-156 (Feb. 1, 2003).
Madian, "Proteomic identification of carbonylated proteins and their oxidation sites." Journal of Proteome Research 9(8): 3766-3780 (Aug. 6, 2010).
Mantile, "Human Clara cell 10-kDa protein is the counterpart of rabbit uteroglobin." Journal of Biological Chemistry 268(27): 20343-20351 (Sep. 25, 1993).
Mukherjee, "Modulation of cellular response to antigens by uteroglobin and transglutaminase." Advances in Experimental Medicine and Biology 231:135-152 (Jan. 1, 1988).
Mukherjee, "Uteroglobin: a novel cytokine?" Cellular and Molecular Life Sciences 55(5): 771-787 (May 1, 1999).
Mukherjee, "Uteroglobin: a steroid-inducible immunomodulatory protein that founded the Secretoglobin superfamily." Endocrine Reviews 28(7): 707-725 (Dec. 1, 2007) Epub: Oct. 4, 2007.
Nagy, "Superoxide-mediated formation of tyrosine hydroperoxides and methionine sulfoxide in peptides through radical addition and intramolecular oxygen transfer." Journal of Biological Chemistry 284(22): 14723-14733 (May 29, 2009).
Nemes, "A novel function for transglutaminase 1: attachment of long-chain omega-hydroxyceramides to involucrin by ester bond formation." Proceedings of the National Academy Sciences of the USA 96(15): 8402-8407 (Jul. 20, 1999).
Nicolas, "Coupe du roi bisection of protein& Spontaneous tetramerization of two peptides that span the sequence of the rabbit uteroglobin monomer." Journal of the American Chemical Society 127(50): 17719-17733 (Dec. 21, 2005).
Ottaviano, "Redox regulation in the extracellular environment." Circulation Journal 72(1): 1-16 (Jan. 1, 2008).
Pedruzzi, "Differentiation of PLB-985 myeloid cells into mature neutrophils, shown by degranulation of terminally differentiated compartments in response to N-formyl peptide and priming of superoxide anion production by granulocyte-macrophage colony-stimulating factor." British Journal of Haematology 117(3): 719-726 (Jun. 1, 2002).
Peter, "Interchain cysteine bridges control entry of progesterone to the central cavity of the uteroglobin dimer." Protein Engineering 5(4): 351-359 (Jun. 1, 1992).
Ramsay "Clara cell secretory protein oxidation and expression in premature infants who develop bronchopulmonary dysplasia." American Journal of Respiratory and Critical Care Medicine 164(1): 155-161 (Jul. 1, 2001).
Shacter, "Quantification and significance of protein oxidation in biological samples." Drug Metabolism Reviews 32(3-4): 307-326 (Aug. 1, 2000).
Shao, "Methionine sulfoxide and proteolytic cleavage contribute to the inactivation of cathepsin G by hypochlorous acid: an oxidative mechanism for regulation of serine proteinases by myeloperoxidase." Journal of Biological Chemistry 280(32): 29311-29321 (Aug. 12, 2005).
Stadtman, "Fenton chemistry. Amino acid oxidation." Journalof Biological Chemistry 266(26): 17201-17211 (Sep. 15, 1991).
Stadtman, "Cyclic oxidation and reduction of protein methionine residues is an important antioxidant mechanism." Molecular and Cellular Biochemistry 234-235(1-2): 3-9 (May 1, 2002).
Thomas, "Preparation and characterization of chloramines." Methods in Enzymology 132: 569-585 (Jan. 1, 1986).
Tien, "Peroxynitrite-mediated modification of proteins at physiological carbon dioxide concentration: pH dependence of carbonyl formation, tyrosine nitration, and methionine oxidation." Proceedings of the National Academy of Sciences USA 96(14): 7809-7814 (Jul. 6, 1999).
Umland, "Refined structure of rat Clara cell 17 kDa protein at 3.0 A resolution." Journal of Molecular Biology 224(2): 141-448 (Mar. 20, 1992).
Umland, "Structure of a human Clara cell phospholipid-binding protein-ligand complex at 1.9 A resolution." Nature Structural Biology 1(8): 538-545 (Aug. 1, 1994).
Van Dalen, "Nitrite as a substrate and inhibitor of myeloperoxidase. Implications for nitration and hypochlorous acid production at sites of inflammation." Journal of Biological Chemistry 275(16): 11638-11644 (Apr. 21, 2000).
Winterbourn, "Modeling the reactions of superoxide and myeloperoxidase in the neutrophil phagosome: implications for microbial killing." Journal of Biological Chemistry 281(52): 39860-39869 (Dec. 29, 2006).
Yan, "Chemical probes for analysis of carbonylated proteins: a review." J Chromatography B Analytical Technology Biomedical Life Sci 879(17-18): 1308-1315 (May 15, 2011).
Yan, "Identification of oxidized proteins based on sodium dodecyl sulfate-polyacrylamide gel electrophoresis, Immunochemical detection, isoelectric focusing, and microsequencing." Analytical Biochemistry 263(1): 67-71 (Oct. 1, 1998).
Yang, "Selective oxidation in vitro by myeloperoxidase of the N-terminal amine in apolipoprotein B-100" Journal of Lipid Research 42(11): 1891-1896 (Nov. 1, 2001).
Yang, "Selective modification of apoB-100 in the oxidation of low density lipoproteins by myeloperoxidase in vitro." Journal of Lipid Research 40(4): 686-698 (Apr. 1, 1999).
International Search Report in PCT/US/1430101 dated Oct. 27, 2014.
Supplementary European Search Report in EP 14 76 3146 dated Sep. 30, 2016.

(56) References Cited

OTHER PUBLICATIONS

Abdel-Latif, "Intratracheal Clara cell secretory protein (CCSP) administration in preterm infants with or at risk of respiratory distress syndrome." Cochrane Database of Systematic Reviews (5):CD008308 May 11, 2011.

Jackson, "Update of the human secretoglobin (SCGB) gene superfamily and an example of 'evolutionary bloom' of androgenbinding protein genes within the mouse Scgb gene superfamily." Human Genomics 5(6):691-702 Oct. 1, 2011.

* cited by examiner

FIG. 1: Human SCGB3A2 amino acid sequences
(aka Hin-2, UGRP1)

```
                 10         20         30         40         50         60         70         80         90
SEQ ID NO 2:     MKLVTFLLV TISLCSYSAT AFLINKVPLP VDKLAPLPLD NILPFMDPLK LLLKTLGISV EHLVEGLRKC VNELGPEASE AVKKLLEALS HLV       Source
                                                                                                                         Genebank AAQ89338

SEQ ID NO 3:              AT AFLINKVPLP VDKLAPLPLD NILPFMDPLK LLLKTLGISV EHLVEGLRKC VNELGPEASE AVKKLLEALS HLV             Clarassance version
                                                                                                                         rhSCGB3A2

Other published sequences 9         19         29         39         49
SEQ ID NO 4:         FLINKVPLP VDKLAPLPLD NILPFMDPLK LLLKTLGISV EHLVEGLRKC VNELGPEASE AVKKLLEALS HLV                      US20050054822 (Consensus)

SEQ ID NO 5:              AFLINKVPLP VDKLAPLPLD NILPFMDPLK LLLKTLGISV EHLVEGLRKC VNELGPEASE AVKKLLEALS HLV                N-terminal prediction tool
                                                                                                                         (www.expasy.org)

SEQ ID NO 6:     MKLVTFLLV TISLCSYSAT AFLINKVPLP VDKLAPLPLD NILPFMDPLK LLLKTLGISV EHLVEGLRKC VNELGPEASE AVKKLLEALS HLV    CA 2,331,934 (2001)

SEQ ID NO 7:              T AFLINKVPLP VDKLAPLPLD NILPFMDPLK LLLKTLGISV EHLVEGLRKC VNELGPEASE AVKKLLEALS HLV              sig pep 1-13 predicted SEQ ID NO 8:              FLINKVPLP VDKLAPLPLD NILPFMDPLK LLLKTLGISV EHLVEGLRKC VNELGPEASE AVKKLLEALS HLV                 sig pep 1-21 predicted SEQ ID NO 9:                  PLPLP NILPFMDPLK LLLKTLGISV EHLVEGLRKC VNELGPEASE AVKKLLEALS HLV                            actual isolated peptide SEQ ID NO 10:             AFLINKVPLP VDKLAPLPLD NILPFMDPLK LLLKTLGISV EHLVEGLRKC VNELGPEASE AVKKLLEALS HLV                actual isolated peptide
```

FIG. 2: SDS-PAGE of purified rhSCGB3A2
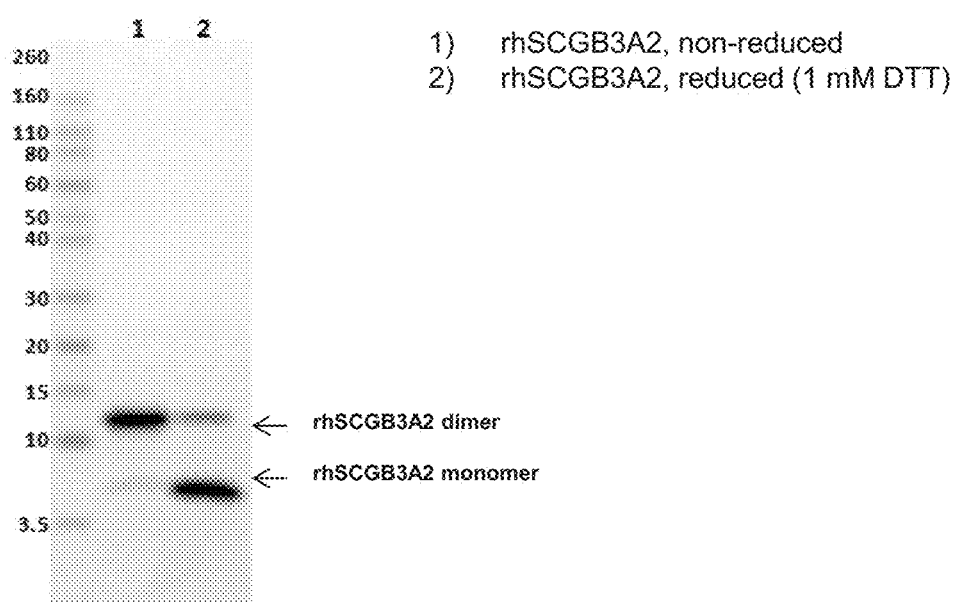

FIG. 3: Isoelectric focusing of purified rhSCGB3A2
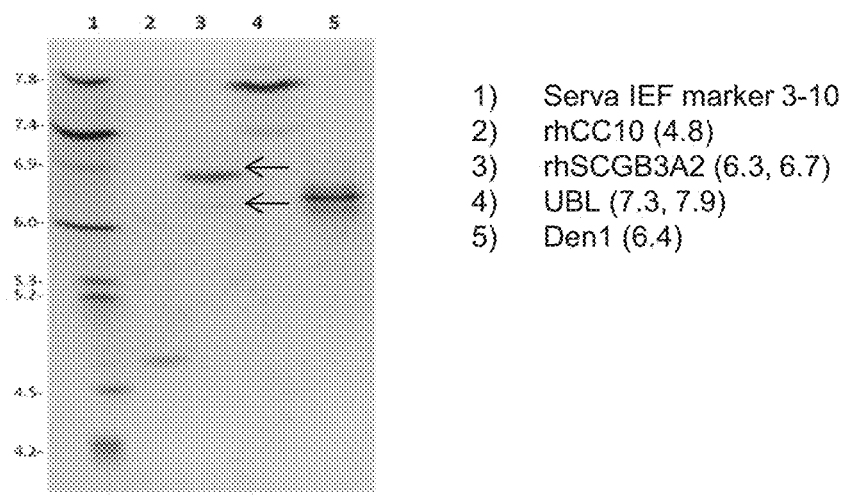
1) Serva IEF marker 3-10
2) rhCC10 (4.8)
3) rhSCGB3A2 (6.3, 6.7)
4) UBL (7.3, 7.9)
5) Den1 (6.4)

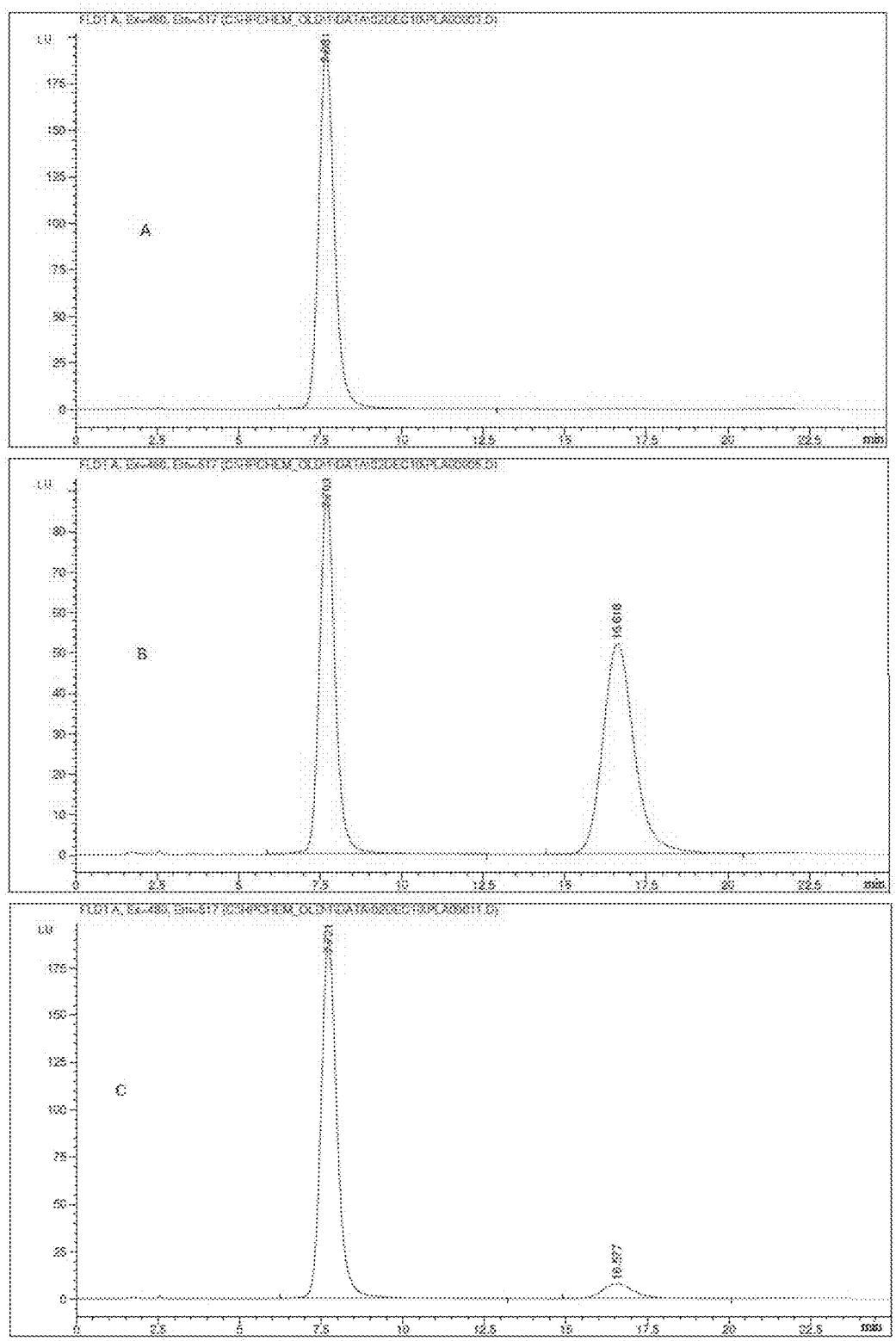
FIG. 4: Inhibition of PLA2 by rhSCGB3A2

FIG. 5: Western blot of SCGB3A2 in human TAF
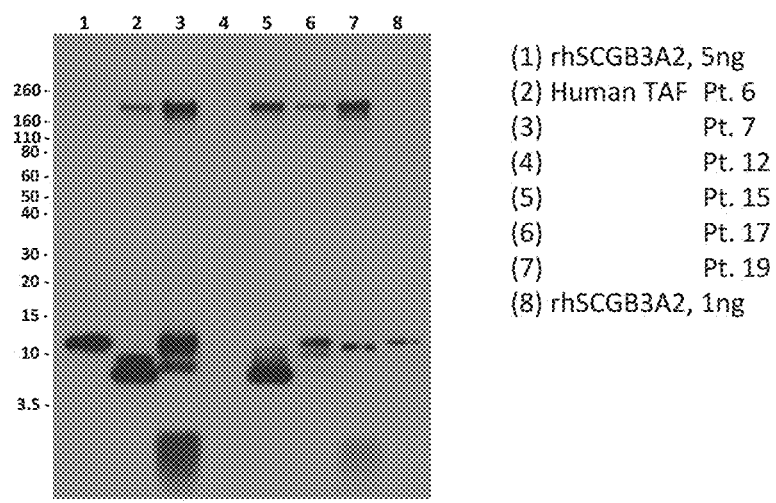

FIG. 6: Standard curve for competitive ELISA for human SCGB3A2
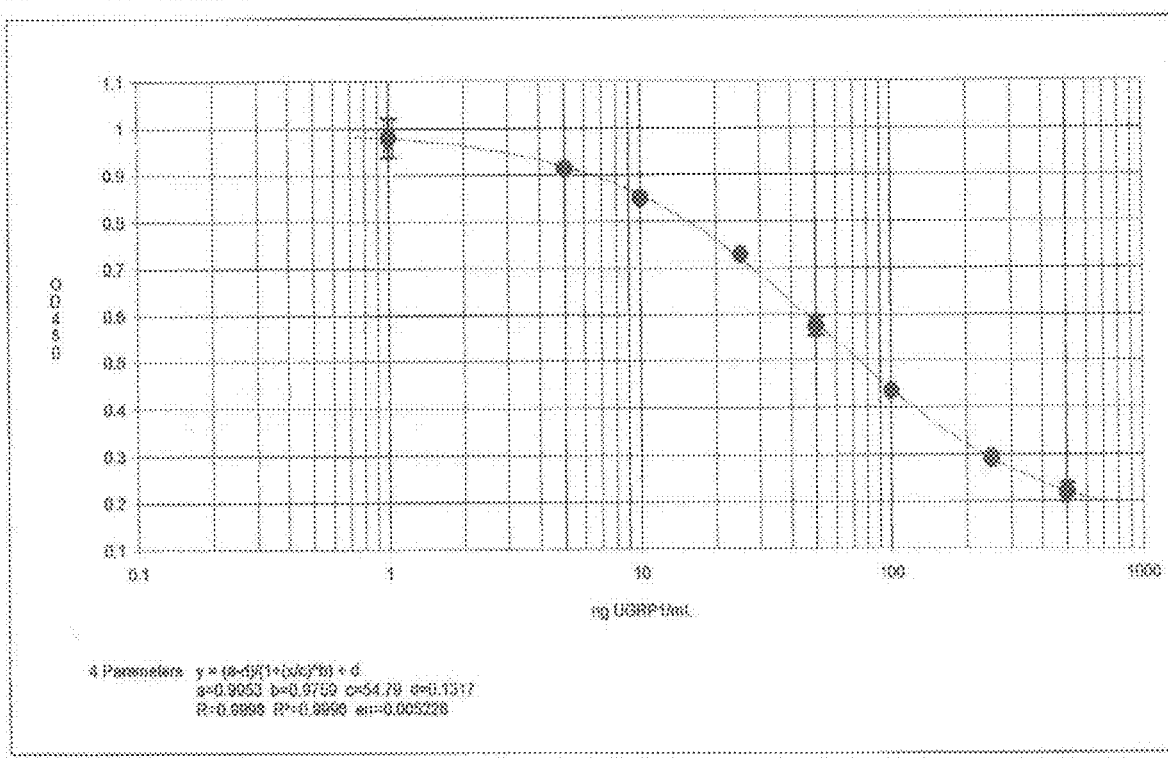
SCGB3A2 (nanograms/ml)

COMPOSITIONS AND METHODS OF USE FOR RECOMBINANT HUMAN SECRETOGLOBINS

CROSS-REFERENCE TO RELATED APPLICATIONS

This application is continuation of U.S. patent application Ser. No. 14/880,908, filed Oct. 12, 2015, which is a divisional of U.S. patent application Ser. No. 13/843,289, filed Mar. 15, 2013, now U.S. Pat. No. 9,765,127, the disclosures of which are hereby incorporated by reference in their entireties.

FIELD OF THE INVENTION

The invention relates to pharmaceutical compositions, methods of production, analytical methods, and methods of use for secretoglobin proteins, including SCGB1A1 (CC10), SCGB3A1, and SCGB3A2. Novel physiologic roles and therapeutic uses for these secretoglobins have been identified. Specifically, the present invention relates to novel methods of use for rhCC10, rhSCGB3A2, and rhSCGB3A1 in preventing or delaying hospitalizations due to severe respiratory exacerbations up to 10 months after a course of treatment. The present also relates to novel methods of production and pharmaceutical compositions of rhSCGB3A2 that is stable and possesses anti-inflammatory properties. More specifically, the invention further provides a method to prevent severe respiratory exacerbations by administering rhCC10. The invention further provides a method for treating bronchiectasis and preventing exacerbations of bronchiectasis by administering rhSCGB3A2. Even more specifically, the invention provides a method for reversing airway remodeling in chronic lung diseases and preventing airway remodeling in acute lung injuries by administering rhCC10, rhSCGB3A2, or rhSCGB3A1. Even more specifically, these secretoglobins modify airway remodeling indirectly by restoring normal numbers of Clara cells and their associated structures, termed neuro-epithelial bodies (aka NEBs) or neuroendocrine cell clusters (aka NECs) that are identified by their immunoreactivity to anti-CGRP1 antibodies, in the airway epithelium. The Clara cells and other CGRP1+ cells, then secrete these secretoglobins and other components of the normal mucosal milieu, contributing to homeostasis and normal functioning of the respiratory mucosa and epithelium that is then more resistant to inhaled challenges without experiencing severe exacerbations.

BACKGROUND OF THE INVENTION secretoglobin 1A1 (SCGB1A1), is one of a family of related proteins called secretoglobins believed to exist in all vertebrate animals. There are two additional secretoglobins that are also expressed at very high levels in the respiratory tract, called SCGB3A1 and SCGB3A2 (Porter, 2002). These three proteins; SCGB1A1, SCGB3A1, and SCGB3A2, are herein referred to as "respiratory secretoglobins." Table 1 shows Genebank loci and amino acid sequences for each respiratory secretoglobin.

TABLE 1

Respiratory secretoglobin proteins

| Protein | Genebank locus | Amino acid sequence |
|---|---|---|
| SCGB1A1 (CC10) | BC004481 | EICPSFQRVIETLLMDTPSSYEAAMELFSPDQDMREAGAQLK KLVDTLPQKPRESIIKLMEKIAQSSLCN (SEQ ID NO: 11) |
| SCGB3A1 | NP_443095 | AAFLVGSAKPVAQPVAALESAAEAGAGTLANPLGTLNPLKL LLSSLGIPVNHLIEGSQKCVAELGPQAVGAVKALKALLGALT VFG (SEQ ID NO: 12) |
| SCGB3A2 | AAQ89338 | ATAFLINKVPLPVDKLAPLPLDNILPFMDPLKLLLKTLGISVE HLVEGLRKCVNELGPEASEAVKKLLEALSHLV (SEQ ID NO: 3) |

The primary source of respiratory secretoglobins in mammals is the pulmonary and tracheal epithelia, especially the non-ciliated bronchiolar airway epithelial cells (primarily Clara cells), and they are very abundant locally-produced proteins in the extracellular fluids of the adult lung. They are also secreted in the nasal epithelia. Thus, respiratory secretoglobins are highly expressed in both the upper and lower respiratory tracts; the upper respiratory tract includes the nasal passages and sinuses and the lower respiratory tract includes the trachea, bronchi, and alveoli of the lungs. A significant amount of respiratory secretoglobins are also present in serum and urine, which is largely derived from pulmonary sources. SCGB3A1 is also expressed in the stomach, heart, small intestine, uterine and mammary glands, and SCGB3A2 is expressed at a low level in the thyroid (Porter, 2002). CC10 is also produced by reproductive tissues (uterus, seminal vesicles), exocrine glands (prostate, mammary gland, pancreas), endocrine glands (thyroid, pituitary, adrenal, and ovary) and by the thymus and spleen (Mukherjee, 1999; Mukherjee, 2007). The major recoverable form of human CC10 in vivo is a homodimer, comprised of two identical 70 amino acid monomers, with an isoelectric point of 4.8. Its molecular weight is 15.8 kDa, although it migrates on SDS PAGE at an apparent molecular weight of about 10 kDa. The monomers are arranged in an antiparallel configuration, with the N-terminus of one adjacent to the C-terminus of the other, and in the fully-oxidized form of the dimer, the monomers are connected by two disulfide bonds (Mukherjee, 1999). However, the in vivo molecular form (monomer, dimer, or other complex) of SCGB3A2 in human samples has not yet been characterized. All three respiratory secretoglobins may be made by synthetic (Nicolas, 2005) or recombinant methods (Mantile, 1993), although there have been no reports to date describing the successful synthesis of human SCGB3A1 and SCGB3A2 and the biochemical characterization of these proteins in vitro.

CC10 is an anti-inflammatory and immunomodulatory protein that has been characterized with respect to various interactions with other proteins, receptors and cell types (reviewed in Mukherjee, 2007, Mukherjee, 1999, and Pilon, 2000). Lower levels of CC10 protein or mRNA have been found in various tissue and fluid samples for a number of clinical conditions characterized by some degree of inflammation including asthma (Lensmar, 2000; Shijubo, 1999; Van Vyve, 1995), pneumonia (Nomori, 1995), bronchiolitis obliterans (Nord, 2002), sarcoidosis (Shijubo, 2000), and in patients suffering from chronic rhinitis with recurrent sinusitis and nasal polyposis (Liu, 2004). Pulmonary epithelial cells, the body's primary source for endogenous CC10, are often adversely affected in these conditions, depleted or even ablated (Shijubo, 1999). CC10 knockout (KO) mice have been important in characterizing the role of CC10 in pulmonary homeostasis, reproduction, and certain types of renal disease. There are two strains of CC10 KO mice, each with different genetic knockout constructs and different parental mouse strains. One knockout strain exhibits several extreme phenotypes, including systemic inflammation, poor reproductive capability (small litter sizes), and a lethal renal phenotype resembling human IgA nephropathy (Zhang, 1997; Zheng, 1999). The other knockout strain does not possess these extreme phenotypes and is more viable, enabling a greater number of experiments to be performed (Stripp, 1997). Both strains of CC10 KO mice share much greater sensitivity and significantly heightened inflammatory responses to pulmonary challenges in models of asthma, pulmonary fibrosis and carcinogenesis, bacterial and viral infections, and oxygen and ozone exposures (Plopper, 2006; Lee, 2006; Yang, 2004; Wang, 2003; Harrod, 2002; Chen, 2001; Wang, 2001; Hayashida, 2000; Harrod, 1998). Restoration of CC10 function in these knockout mice using recombinant human CC10 (rhCC10) has been shown to mitigate the exaggerated pulmonary inflammatory responses in short term challenge models with endpoints of up to 7 days (Chen, 2001; Wang, 2003). Most relevant to the invention, both strains share an airway epithelial phenotype characterized by significantly decreased numbers of Clara cells and associated structures called neuro-epithelial bodies (NEBs; Castro, 2000) or neuroendocrine cell clusters (NECs; Hong, 2001; Reynolds, 2000), as identified by positive staining with calcitonin-gene related protein 1 (CGRP1). These 2-10 fold deficiencies in Clara cells and associated structures in the airways arise in the absence of any type of injury in these KO mice.

Premature infants who experience respiratory distress syndrome (RDS) are deficient in native CC10. In a clinical trial, a single dose of rhCC10 was administered on the day of birth and mediated potent short-term anti-inflammatory effects for 3-7 days in the lungs. Pharmacokinetic analyses showed that surplus CC10 was cleared within 48 hours of the single dose administered. Despite the anti-inflammatory effects, rhCC10 did not prevent development of neonatal bronchopulmonary dysplasia (BPD) (Levine, 2005), as defined by clinical parameters, including 1) opacity of chest X-ray at 28 days after birth or 2) use of supplemental oxygen at 36 weeks of postmenstrual age (PMA). Nor did rhCC10 reduce the time in the hospital or the number of days on the ventilator, despite the significant reductions in indices of pulmonary inflammation observed in tracheal aspirate fluids (TAF). There were no differences between the placebo, low dose and high dose treatment groups the 12 month endpoint, as stated in Levine et al. (2005).

Premature infants with BPD are predisposed towards experiencing frequent and severe respiratory exacerbations and their re-hospitalization rates in the first 1-2 years of life are high. Severe respiratory exacerbations are characterized by shortness of breath, labored breathing, nasal and chest congestion, overproduction of mucus, and sometimes respiratory distress. Severe respiratory exacerbations occur when patients encounter environmental exposures and infections through inhalation of dust, smoke, allergens, pollutants, chemicals, bacteria, fungi, and viruses.

Many types of patients with chronic diseases of the respiratory, gastrointestinal, urogenital tracts are susceptible to severe exacerbations when exposed to an environmental trigger. Likewise, patients with immunologic diseases, including autoimmune and allergic diseases, are also susceptible to severe exacerbations when exposed to an environmental trigger. Severe or acute exacerbations are considered frequent when they occur more than 3 times per year in a patient. Even patients who do not have a chronic disease, but who experience acute lung injury (ALI), are susceptible to frequent and severe acute respiratory episodes, resembling severe respiratory exacerbations, following the injury. Environmental irritants that trigger exacerbations include, but are not limited to, dust, particulates, smoke, allergens, pollutants, chemicals, contaminants, bacteria, fungi, and viruses may be inhaled, ingested, swallowed, absorbed through the skin, or otherwise come in contact topically with a wet mucosal surface of the patient's body.

OBJECTS OF THE INVENTION

The foregoing provides a non-exclusive list of the objectives achieved by the present invention:

It is a primary object of the invention to administer a secretoglobin to prevent hospitalization due to a severe exacerbation of an underlying or chronic disease for up to 10 months after the secretoglobin is administered.

It is a further object of the invention to administer a respiratory secretoglobin to prevent hospitalization due to a severe exacerbation of an underlying or chronic respiratory disease for up to 10 months after the secretoglobin is administered.

It is a further object of the invention to administer rhCC10 to prevent hospitalization due to a severe exacerbation of an underlying or chronic respiratory disease for up to 10 months after the secretoglobin is administered.

It is a further object of the invention to administer rhSCGB3A2 to prevent hospitalization due to a severe exacerbation of an underlying or chronic respiratory disease for up to 10 months after the secretoglobin is administered.

It is a further object of the invention to administer rhSCGB3A1 to prevent hospitalization due to a severe exacerbation of an underlying or chronic respiratory disease for up to 10 months after the secretoglobin is administered.

It is a further object of the invention to administer a secretoglobin to prevent hospitalization due to a severe exacerbation of an underlying or chronic disease for at least one month after the secretoglobin is administered.

It is a further object of the invention to administer a respiratory secretoglobin to prevent hospitalization due to a severe exacerbation of an underlying or chronic respiratory disease for at least one month after the secretoglobin is administered.

It is a further object of the invention to administer rhCC10 to prevent hospitalization due to a severe exacerbation of an underlying or chronic respiratory disease for at least one month after the secretoglobin is administered.

It is a further object of the invention to administer rhSCGB3A2 to prevent hospitalization due to a severe exacerbation of an underlying or chronic respiratory disease for at least one month after the secretoglobin is administered.

It is a further object of the invention to administer rhSCGB3A1 to prevent hospitalization due to a severe exacerbation of an underlying or chronic respiratory disease for at least month after the secretoglobin is administered.

It is a further object of the invention to administer a secretoglobin to increase the time interval from one severe exacerbation to the next, in patients who typically experience recurrent exacerbations of chronic diseases.

It is a further object of the invention to increase the time interval from one severe exacerbation to the next, for up to 10 months after a dose or course of respiratory secretoglobin therapy, in patients who experience recurrent exacerbations of chronic diseases.

It is a further object of the invention to administer a respiratory secretoglobin to increase the time interval from one severe respiratory exacerbation to the next, in patients who experience recurrent exacerbations of chronic respiratory diseases.

It is a further object of the invention to administer a respiratory secretoglobin to prevent a severe acute respiratory episode resembling an exacerbation in a patient who experienced an acute lung injury but was not diagnosed with a chronic respiratory disease prior to the injury.

It is a further object of the invention to administer a respiratory secretoglobin to prevent a severe exacerbation after exposure to an inhaled irritant capable of triggering an exacerbation, in a susceptible patient with a chronic respiratory disease.

It is a further object of the invention to administer a secretoglobin to increase the time interval from one severe autoimmune exacerbation to the next, in patients who experience recurrent exacerbations of chronic autoimmune diseases.

It is a further object of the invention to administer a respiratory secretoglobin to increase the time interval from one severe respiratory exacerbation to the next, in patients who experience frequent exacerbations of chronic respiratory diseases.

It is a further object of the invention to administer a respiratory secretoglobin to increase the time interval from one severe autoimmune exacerbation to the next, in patients who experience frequent exacerbations of chronic autoimmune diseases.

It is a further object of the invention to administer the secretoglobin during or after the previous exacerbation in order to prevent the next exacerbation.

It is a further object of the invention to administer the secretoglobin by intravenous injection, intratracheal instillation, inhalation, intranasal instillation, orally, sublingually, or by anal or vaginal cream, gel, or suppository.

It is a secondary object of the invention to administer a respiratory secretoglobin to increase numbers of non-ciliated secretory epithelial cells and thereby rehabilitate mucosal tissues.

It is a further object of the invention to administer a respiratory secretoglobin to increase numbers of non-ciliated secretory epithelial cells in the respiratory tract, including the upper and lower respiratory tract, and thereby rehabilitate respiratory mucosal tissues and airways.

It is a further object of the invention to administer a respiratory secretoglobin to increase numbers of Clara cells in the respiratory tract and thereby rehabilitate respiratory mucosal tissues and airways.

It is a further object of the invention to administer a respiratory secretoglobin to increase numbers of NEBs and NECs in the respiratory tract and thereby rehabilitate respiratory mucosal tissues and airways.

It is a further object of the invention to administer a respiratory secretoglobin to increase the amount of one or more native respiratory secretoglobins circulating in the blood.

It is a further object of the invention to administer a respiratory secretoglobin to increase the amount of one or more native respiratory secretoglobins found in respiratory airway lining fluids (ALF) of the nasal passages, trachea, or lungs and/or sputum or induced sputum.

It is a further object of the invention to administer a respiratory secretoglobin to increase numbers of secretoglobin-secreting cells in the respiratory tract and thereby rehabilitate respiratory mucosal tissues and airways.

It is a further object of the invention to administer a respiratory secretoglobin to increase numbers of CC10-secreting cells in the respiratory tract and thereby rehabilitate respiratory mucosal tissues and airways.

It is a further object of the invention to administer a respiratory secretoglobin to increase numbers of SCGB3A2-secreting cells in the respiratory tract and thereby rehabilitate respiratory mucosal tissues and airways.

It is a further object of the invention to administer a respiratory secretoglobin to increase numbers of SCGB3A1-secreting cells in the respiratory tract and thereby rehabilitate respiratory mucosal tissues and airways.

It is a further object of the invention to administer a respiratory secretoglobin to increase numbers of CC10-secreting epithelial cells in the female urogenital tract and thereby rehabilitate vaginal mucosal tissues.

It is a further object of the invention to administer a respiratory secretoglobin to increase numbers of CC10-secreting epithelial cells in the gastrointestinal tract, including the mouth, throat, esophagus, stomach, pancreas, the bile duct, the upper and lower intestines, and the colon, and thereby rehabilitate gastrointestinal mucosal tissues.

It is a further object of the invention to provide a pharmaceutical composition of human SCGB3A2 with a non-native N-terminus of ATA.

It is a further object of the invention to provide a pharmaceutical composition of human SCGB3A2 with an isoelectric point of 6.7.

It is a further object of the invention to provide a pharmaceutical composition of human SCGB3A2 with an isoelectric point of 6.3.

It is a further object of the invention to provide a pharmaceutical composition of human SCGB3A2 with a combination of isoforms with isoelectric points of 6.3 and 6.7.

It is a further object of the invention to provide a pharmaceutical composition of recombinant human SCGB3A2 that is synthesized as a fusion with another protein.

It is a further object of the invention to provide a pharmaceutical composition of recombinant human SCGB3A2 that is synthesized as a fusion with an ubiquitin-like protein.

It is a further object of the invention to administer a human respiratory secretoglobin to delay or prevent an exacerbation of bronchiectasis in a patient diagnosed with bronchiectasis.

It is a further object of the invention to administer a human respiratory secretoglobin to delay or prevent an exacerbation of pulmonary fibrosis in a patient diagnosed with a type of pulmonary fibrosis.

It is a further object of the invention to administer a human respiratory secretoglobin to delay or prevent an exacerbation of cystic fibrosis in a patient diagnosed with a type of cystic fibrosis.

It is a further object of the invention to administer a human respiratory secretoglobin to delay or prevent an exacerbation of COPD in a patient diagnosed with COPD.

It is a further object of the invention to administer a human respiratory secretoglobin to delay or prevent an exacerbation of chronic bronchitis in a patient diagnosed with chronic bronchitis.

It is a further object of the invention to administer a human respiratory secretoglobin to delay or prevent an exacerbation of emphysema in a patient diagnosed with emphysema.

It is a further object of the invention to administer a human respiratory secretoglobin to delay or prevent an exacerbation of asthma in a patient diagnosed with asthma.

It is a further object of the invention to administer a human respiratory secretoglobin to delay or prevent an exacerbation of BPD in a patient diagnosed with BPD.

It is a further object of the invention to administer a human respiratory secretoglobin to delay or prevent an exacerbation of meconium aspiration syndrome (MAS) in a patient diagnosed with MAS.

It is a further object of the invention to administer human CC10 to delay or prevent an exacerbation of bronchiectasis in a patient diagnosed with bronchiectasis.

It is a further object of the invention to administer human CC10 to delay or prevent an exacerbation of pulmonary fibrosis in a patient diagnosed with a type of pulmonary fibrosis.

It is a further object of the invention to administer human CC10 to delay or prevent an exacerbation of cystic fibrosis in a patient diagnosed with a type of cystic fibrosis.

It is a further object of the invention to administer human CC10 to delay or prevent an exacerbation of COPD in a patient diagnosed with COPD.

It is a further object of the invention to administer human CC10 to delay or prevent an exacerbation of chronic bronchitis in a patient diagnosed with chronic bronchitis.

It is a further object of the invention to administer human CC10 to delay or prevent an exacerbation of emphysema in a patient diagnosed with emphysema.

It is a further object of the invention to administer human CC10 to delay or prevent an exacerbation of asthma in a patient diagnosed with asthma.

It is a further object of the invention to administer human CC10 to delay or prevent an exacerbation of BPD in a patient diagnosed with BPD.

It is a further object of the invention to administer human CC10 to delay or prevent an exacerbation of meconium aspiration syndrome (MAS) in a patient diagnosed with MAS.

It is a further object of the invention to administer human SCGB3A2 to delay or prevent an exacerbation of bronchiectasis in a patient diagnosed with bronchiectasis.

It is a further object of the invention to administer human SCGB3A2 to delay or prevent an exacerbation of pulmonary fibrosis in a patient diagnosed with a type of pulmonary fibrosis.

It is a further object of the invention to administer human SCGB3A2 to delay or prevent an exacerbation of cystic fibrosis in a patient diagnosed with a type of cystic fibrosis.

It is a further object of the invention to administer human SCGB3A2 to delay or prevent an exacerbation of COPD in a patient diagnosed with COPD.

It is a further object of the invention to administer human SCGB3A2 to delay or prevent an exacerbation of chronic bronchitis in a patient diagnosed with chronic bronchitis.

It is a further object of the invention to administer human SCGB3A2 to delay or prevent an exacerbation of emphysema in a patient diagnosed with emphysema.

It is a further object of the invention to administer human SCGB3A2 to delay or prevent an exacerbation of asthma in a patient diagnosed with asthma.

It is a further object of the invention to administer human SCGB3A2 to delay or prevent an exacerbation of BPD in a patient diagnosed with BPD.

It is a further object of the invention to administer human SCGB3A2 to delay or prevent an exacerbation of meconium aspiration syndrome (MAS) in a patient diagnosed with MAS.

It is a further object of the invention to administer human SCGB3A1 to delay or prevent an exacerbation of bronchiectasis in a patient diagnosed with bronchiectasis.

It is a further object of the invention to administer human SCGB3A1 to delay or prevent an exacerbation of pulmonary fibrosis in a patient diagnosed with a type of pulmonary fibrosis.

It is a further object of the invention to administer human SCGB3A1 to delay or prevent an exacerbation of cystic fibrosis in a patient diagnosed with a type of cystic fibrosis.

It is a further object of the invention to administer human SCGB3A1 to delay or prevent an exacerbation of COPD in a patient diagnosed with COPD.

It is a further object of the invention to administer human SCGB3A1 to delay or prevent an exacerbation of chronic bronchitis in a patient diagnosed with chronic bronchitis.

It is a further object of the invention to administer human SCGB3A1 to delay or prevent an exacerbation of emphysema in a patient diagnosed with emphysema.

It is a further object of the invention to administer human SCGB3A1 to delay or prevent an exacerbation of asthma in a patient diagnosed with asthma.

It is a further object of the invention to administer human SCGB3A1 to delay or prevent an exacerbation of BPD in a patient diagnosed with BPD.

It is a further object of the invention to administer human SCGB3A1 to delay or prevent an exacerbation of meconium aspiration syndrome (MAS) in a patient diagnosed with MAS.

SUMMARY OF THE INVENTION

Secretoglobin proteins that are expressed in the respiratory tract facilitate development of Clara cells and other respiratory epithelial cells and resident immune structures in the functional respiratory epithelium. There are three secretoglobins that are highly expressed in the human respiratory tract, including SCGB1A1 (aka CC10, uteroglobin, CCSP, CC16, etc.), SCGB3A2 (aka UGRP1, HIN-2) and SCGB3A1 (aka UGRP2, HIN-1).

The invention generally pertains to the use of respiratory secretoglobins to delay and prevent severe exacerbations of chronic diseases caused by environmental exposures, particularly respiratory diseases. At the tissue level, the respiratory secretoglobins mediate an increase in the numbers of secretoglobin-secreting cells and associated structures in respiratory tissues, which may be measured indirectly through increases in the amounts of their secretoglobin secretion products in body fluids. For example, rhCC10 administration mediates an increase in the number of Clara cells, NEBs, and NECs, restoring the respiratory airway epithelia. At present, this is the only hypothesis that is consistent with the airway epithelial phenotype of CC10 KO mice and explains the data in premature infants pertaining to very strong long-term protection from severe respiratory exacerbations, but not prevention of neonatal BPD, which is a type of pulmonary fibrosis.

Although rhCC10 did not avert the development of neonatal BPD, it did confer long-term protection from severe respiratory exacerbations requiring re-hospitalization was observed at 6 months PMA, which is the time at which the infant would have been 6 months old after 40 weeks gestation. Since the trial enrolled infants between 24-28 weeks PMA, this endpoint is up to 10 months after a single dose of rhCC10.

BRIEF DESCRIPTION OF THE DRAWINGS

FIG. 1: Human SCGB3A2 amino acid sequences, alignment of human SCGB3A2 amino acid sequences with comparison of predicted and actual N-termini FIG. 2: SDS-PAGE of purified rhSCGB3A2, SDS-PAGE of purified rhSCGB3A2. Samples containing 5 micrograms each with and without 1 mM DTT were mixed with SDS Sample Buffer, boiled 5 minutes and loaded on a 10-20% tricine gel. The gel was run and stained with Coomassie R250. The gel was de-stained and imaged with a digital camera.

FIG. 3: Isoelectric focusing of purified rhSCGB3A2, Isoelectric focusing of purified rhSCGB3A2, compared to rhCC10 and UBL and Den-1. Samples containing 5 micrograms each were loaded on a Novex IEF gel. The gel was run and stained with Coomassie R250. The gel was de-stained and imaged with a digital camera. Arrows represent major and minor isoforms of rhSCGB3A2 with ATA N-terminus.

FIG. 4: In vitro inhibition of sPLA$_2$-1B with rhSCGB3A2 Panel A: UNIBIPY substrate; no PLA$_2$; no rhSCGB3A2. Panel B: UNIBIPY substrate plus PLA$_2$; no rhSCGB3A2. Panel C: UNIBIPY substrate plus PLA2 plus rhSCGB3A2. Peak #1 is the UNIBIPY phospholipid substrate, peak #2 is the product after cleavage by sPLA$_2$.

FIG. 5: Western blot of SCGB3A2 in human TAF. Western blot of tracheal aspirate fluids from human infants compared to purified rhSCGB3A2 using anti-rhSCGB3A2 rabbit polyclonal antibody. Samples containing 20 microliters of each TAF were loaded on a Novex 10-20% tricine gel; rhSCGB3A2 is in lane 1 (5 nanograms) and lane 8 (1 nanogram). The gel was de-stained and imaged with a digital camera.

FIG. 6: A standard curve of an ELISA for rhSCGB3A2 is depicted.

DETAILED DESCRIPTION

Three pieces of evidence were combined to conceive the invention; including 1) the long term protection from severe respiratory exacerbations and re-hospitalization by a single dose of rhCC10 observed in premature infants, 2) the airway epithelial phenotypes of CC10 KO mice, and 3) the "growth factor" properties of SCGB3A2 (Guha, 2012; Kurotani, 2008; Kurotani, 2008a; Inoue, 2008; Niimi, 2001). Despite many years of research, there is no public consensus concerning the role of CC10 in the respiratory epithelium, other than that it mediates anti-inflammatory effects. A recent clinical trial failure in a nasal allergen challenge model of allergic rhinitis demonstrated that the even its anti-inflammatory effects in vivo are not consistent against all types of inflammatory disease (Widegren, 2009). And, despite a complete CC10 deficiency, Clara cells are still found in the airways of both strains of CC10 KO mice. Although CC10 and SCGB3A2 are structurally similar, and, therefore, believed to share some functions, there are no reports pertaining to the stimulation of growth or development of airway epithelial cells by CC10, and rhCC10 is, in fact, well-known to suppress the growth of tumor cells of epithelial origin (Kundu, 1996; Leyton, 1994), including an airway epithelial cell line, A549 (Szabo, 1998).

We nevertheless believe that the rhCC10 administered to premature infants on the day of birth stimulated the development of CC10-secreting cells, which, in turn, produced native CC10, which stimulated development of more CC10-secreting cells, and so on. The end result was a more normal and resilient respiratory epithelium in the rhCC10-treated infants who were more resistant to all environmental challenges (dust, smoke, allergens, RSV infection, influenza infection, etc.) compared to the placebo-treated infants. A single dose of rhCC10 on the day of birth conferred 100% protection from re-hospitalization due to severe respiratory exacerbation, contrasting the 50% re-hospitalization rate observed in the placebo-treated infants.

We further believe that the use of CC10 to stimulate development of CC10-secreting cells in the respiratory epithelium will also work in adults with chronic respiratory diseases in which airway remodeling has resulted in loss of Clara cells. A course of treatment with rhCC10 may not cure the disease, but, we believe, would restore, to some extent, Clara cells and associated structures, resulting in a more normal epithelium that is then more resistant to subsequent environmental challenges. The clinical outcome of a course of rhCC10 treatment would then be an increase in the time interval to the next severe exacerbation.

We further believe that the airway epithelial phenotype of Clara cell deficiency in CC10 KO mice suggests that CC10 is an autocrine and paracrine factor required for the development of Clara cells, associated structures, and other normal cell populations of the airway epithelium. We believe that CC10 is an autocrine and paracrine factor required for the development and maintenance of CC10-secreting cells outside of the respiratory tract, including the gastrointestinal tract and urogenital tract. There is much speculation that because secretoglobins share structural similarities that they will also share similar function, however, no biological activity has ever been previously shown to be shared between any two secretoglobins either in vitro or in vivo. Herein, we report that rhSCGB3A2 shares with CC10, the ability to inhibit porcine pancreatic phospholipase A$_2$ in vitro. This is the first report that any other secretoglobin, besides CC10, actually inhibits any phospholipase A$_2$ enzyme or possesses any type of anti-inflammatory activity. Based on these results, we infer that other secretoglobins, including respiratory secretoglobins, which share structural similarities with rhCC10, can stimulate the development and maintenance of the cells that secrete them to effect long-term clinical benefits such as increased time to next exacerbation, decreased severity of next exacerbation, and prevention of severe exacerbations following acute injury.

EXAMPLES

Example 1: Long Term Protection by rhCC10 in Premature Infants with RDS

The safety, pharmacokinetics, and anti-inflammatory properties of rhCC10 were evaluated in a randomized, placebo-controlled, double-blinded, multicenter trial of 22 premature infants with respiratory distress syndrome (RDS) with mean birth weight of 932 g and mean gestational age of 26.9 wks, who received one intratracheal (IT) dose of placebo (n=7), 1.5 mg/kg (n=8) or 5.0 mg/kg (n=7) of rhCC10 following surfactant treatment (Levine, 2005). rhCC10-treated infants showed significant reductions in TAF total cell counts (P<0.001), neutrophil counts (P<0.001), and total protein concentrations (P<0.01) and decreased IL-6 (P<0.07) over the first 3 days of life. The rhCC10 was safe and well tolerated.

Remarkably, and despite small numbers, follow-up of 17 infants at 6 months corrected gestational age (CGA) found that 0/11 who received rhCC10 were re-admitted to the hospital for respiratory causes compared to 3/6 receiving placebo as shown in Table 2 (P<0.05 Fisher's Exact Test, two tailed).

TABLE 1

Re-hospitalizations for severe respiratory exacerbations

|  | 6 months CGA |
|---|---|
| Placebo (7 enrolled) | 3/6 |
| 1.5 mg/kg (8 enrolled) | 0/6 |
| 5 mg/kg (7 enrolled) | 0/5 |

This result is even more remarkable when considering that 6 months CGA, in this context, means a time period corresponding to 6 months after the infant would have been 40 weeks gestation, and that some infants in the study were 24 weeks post-menstrual age (PMA) at birth, so that the 6 month CGA follow up timepoint occurred as many as 10 months after a single dose of rhCC10 administered on the day of birth. From a statistical standpoint, the results demonstrate at least a 57% incidence of re-hospitalization in the placebo group versus at least a 27% in the rhCC10 group. This is a very powerful long-term effect and these data illustrate a significant and unprecedented long-term benefit for administration of rhCC10.

It is even more remarkable to find such a profound long term benefit when pharmacokinetic analyses showed that the excess CC10 was eliminated within 48 hours of administration, with a serum half-life of 9-11 hours (Levine, 2005). A significant amount of rhCC10 was observed in the tracheal aspirate fluids for nearly 2 days, and reached the serum by 6 h, but was then filtered by the kidney and excreted in urine by 12 h. The rhCC10 followed the natural physiological distribution path from lung to blood to urine and demonstrated long-term benefits, despite the rapid elimination.

Example 2: Cloning and Expression of rhSCGB3A2

FIG. 1 shows the amino acid sequence of rhSCGB3A2 that was made for these studies. The sequence was taken from Genebank locus AAQ89338. As a result of the recombinant product method that utilized an ubiquitin-like (UBL) fusion system and released the rhSCGB3A2 product from the UBL using a UBL-protease, the N-terminus differs from the N-termini predicted for the native protein using consensus single peptide cleavage sites for mammalian secreted proteins. It also differs from the N-termini of actual peptides isolated from human fluid samples. This is the first description of the synthesis of human SCGB3A2 without a histidine purification tag and the effects of the N-terminus on the stability and activity of the protein could not be predicted.

The amino acid sequence of rhSCGB3A2 was shown in Table 1 and has predicted molecular weight of 8147.82 Daltons and a predicted isoelectric point of 6.1.

A synthetic DNA coding sequence for rhSCGB3A2 was designed using jcat (www.jcat.de), with codon usage optimized for expression in *E. coli* bacteria K12 strain. Once the DNA sequence was generated, restriction sites were added to the ends to facilitate directional cloning of the gene into the bacterial expression vector, pTXB1, already containing the UBL. SCGB3A2 was cloned as a C-terminal extension of the UBL. An AflII site was placed at the 5' end and a BamHI site was placed at the 3' end for directional cloning.

The new gene for rhSCGB3A2 was synthesized from overlapping oligonucleotides using PCR. The DNA sequence for the rhSCGB3A2 gene is SEQ ID NO 1:

CTTAAGAGGTGGTGCTACCGCTTTCCTGATCAACAAAGTTCCGCTGCCGG

TTGACAAACTGGCTCCGCTGCCGCTGGACAACATCCTGCCGTTCATGGAC

CCGCTGAAACTGCTGCTGAAAACCCTGGGTATCTCTGTTGAACACCTGGT

TGAAGGTCTGCGTAAATGCGTTAACGAACTGGGTCCGGAAGCTTCTGAAG

CTGTTAAAAAACTGCTGGAAGCTCTGTCTCACCTGGTTTAGTAAGGATCC

The pTXB1 plasmid containing the UBL-rhSCGB3A2 fusion was transformed into *E. coli* strain HMS174/DE3 which contains a DE3 prophage encoding the T7 RNA polymerase that enables inducible expression of the fusion protein. Colonies were screened for expression of the fusion protein and the rhSCGB3A2 gene was reconfirmed by DNA sequencing in high expressers.

A four liter fermentation culture containing SuperBroth media with ampicillin was inoculated from a 120 ml overnight culture of the highest-expressing clone and grown at 37° C. The culture was induced to overexpress the UBL-rhSCGB3A2 fusion protein at an $OD_{600}$ of 8.75 using 0.3 mM IPTG, then allowed to grow for another 2 hours. Cell paste was harvested by centrifugation and the wet cell paste yield was 67 grams. The cell paste was then used for purification of rhSCGb3A2.

Example 3: Purification of rhSCGB3A2

The cell paste was resuspended in 20 mM $NaH_2PO_4$, 0.5 M NaCl, pH 7.2, then the cells were ruptured by freeze-thaw to generate a crude lysate. The crude lysate was clarified by centrifugation at 19,800×g for 20' at 4° C. DNA, endotoxin, and other bacterial contaminants were precipitated out of the clarified lysate supernatant using polyethylimine (PEI) at a concentration of 0.025% and a second centrifugation at 19,800×g for 10' at 4° C. The PEI supernatant was then filtered through a 0.22 micron filter and 10 mM imidazole was added to the filtrate. Both the UBL and the UBL protease contain a histidine tag so that they bind to an immobilized metal affinity chromatography column. The filtrate containing the UBL-rhSCGB3A2 fusion protein was then passed over an IMAC column (nickel chelating sepharose fast flow) previously equilibrated in 20 mM $NaH_2PO_4$, 0.5 M NaCl, 10 mM imidazole, pH 7.2, the column was washed with the same buffer, then the UBL-rhSCGB3A2 fusion protein was eluted with 20 mM $NaH_2PO_4$, 100 mM NaCl, 300 mM imidazole, pH 7.2. The IMAC eluate was then concentrated and buffer exchanged using tangential flow filtration with a 5 kDa NMWCO filter in 15 mM Tris, 15 mM BisTris, 40 mM NaCl, pH 7.0. The UBL-rhSCGB3A2 was further purified over a Macro Prep High Q column (BioRad) in which contaminants were bound and the UBL-rhSCGB3A2 flowed through. The rhSCGB3A2 was then separated from the UBL by digestion with UBL protease Den-1 (1:100 molar ratio) in 5 mM DTT, with pH adjusted to 6.5 with HCl, at 37° C. for 2 hours. The rhSCGB3A2 was then purified from the digestion mixture using cation exchange chromatography (GE Sepharose SP High Performance). The SP column was equilibrated with 15 mM Tris, 15 mM BisTris, 40 mM NaCl, pH 6.5, the digestion mixture loaded, and contaminants bound to the column while rhSCGB3A2 flowed through. The SP flow through was then extensively dialyzed against 0.9% NaCl using a 3.5 kDa MWCO regenerated cellulose membrane. The sample was concentrated using centrifugal concentrators (3.5 kDa MWCO), then filtered through a 0.22 micron filter. The filtrate was purified rhSCGB3A2. FIG. 2 shows SDS-PAGE analysis of the final purified protein. It is >97% pure by densitometry of SDS-PAGE, and roughly 95% dimer and 5% monomer. As with rhCC10, it is difficult to completely reduce the dimer to monomer with reducing agents.

Example 4: Isoelectric Point of rhSCGB3A2

The isoelectric point (pI) of a protein is a measure of the total surface charge of that protein. pI is measured using standard isoelectric focusing (IEF) methods. Approximately 5 micrograms of rhSCGB3A2, rhCC10, UBL, and Den-1 were loaded onto an IEF gel (Novex) in order to determine the pI of rhSCGB3A2 as shown in FIG. 3. When a protein migrates as a single band on SDS-PAGE and multiple bands are observed in the IEF gel, alternate isoforms of the protein are likely present. In contrast to rhCC10, which shows a single band at pI 4.8, rhSCGB3A2 shows two bands at pI 6.7 and 6.3. The predicted pI of our rhSCGB3A2 sequence is 6.1 (www.expasy.edu; Protein tool "Compute MW/pI"), yet the vast majority of the protein migrates at a position corresponding to a pI of 6.7. Not even the minor band at 6.3 corresponds to the predicted pI of 6.1. That there are two rhSCGB3A2 IEF bands means that either alternatively folded isoforms are present or that they represent monomers and dimers, as visualized in non-reducing SDS-PAGE. These pIs further show that this preparation is an unknown and unpredicted isoform of rhSCGB3A2 that is unique. The unique folding pattern of a recombinant protein is often determined by the synthetic process, in this case, the selection of N-terminus, expression of the protein as a C-terminal fusion with an ubiquitin-like protein, IMAC purification of the fusion protein, cleavage of the SCGB3A2 from the UBL, and separation of the SCGB3A2 from the UBL and UBL-protease. Thus, the uniqueness of this preparation may be due to the synthetic process, the non-native N-terminus, or a combination of these or other unknown factors.

Example 5: Inhibition of PLA$_2$ by rhSCGB3A2

The biological activity of rhSCGB3A2 was evaluated in a fluorescent and quantitative HPLC assay that evaluates inhibition of porcine pancreatic secretory PLA$_2$ enzyme (sPLA$_2$) that was developed to evaluate the potency of different batches of rhCC10. Inhibition of PLA$_2$ enzymes is thought to be a major anti-inflammatory mechanism of action for CC10. Many have speculated that other secretoglobins may also inhibit PLA$_2$ enzymes, due to their structural similarities with CC10. The rhSCGB3A2 (5.5 micrograms) was mixed with of 100 nanograms porcine sPLA$_2$ 1B (0.1 microgram) and incubated at 37° C. The reaction was started through the addition of the fluorescent phospholipid analogue 2-decanoyl-1-(O-(11-(4,4-difluoro-5,7-dimethyl-4-bora-3a,4a-diaza-s-indacene-3-propionyl)amino)unde-cyl)-sn-glycero-3-phosphocholine (aka UNIBIPY; 47.6 nanograms). After 15 minutes the reaction was terminated by the addition of 2-propanol/n-hexane. The cleavage product was separated from the substrate on a Waters Spherisorb silica HPLC column. The separation was followed with a G1321A fluorescence detector.

Results of the assay are shown in FIG. 4. Panel A shows the UNIBIPY substrate without sPLA$_2$ or rhSCGB3A2; panel B shows the UNIBIPY substrate plus sPLA$_2$, and panel C shows the UNIBIPY substrate plus sPLA$_2$ plus rhSCGB3A2. The sPLA$_2$ cleaves the substrate (peak #1), giving rise to a product (peak #2). In the presence of rhSCGB3A2, the product peak is significantly reduced. Each reaction set was run in duplicate. The rhSCGB3A2 showed 83% inhibition of sPLA$_2$-1B activity in the assay, which is comparable to rhCC10 protein (data not shown).

Percent inhibition is calculated as follows:

$$\% \text{ inhibition} = \{1-(\text{average of the cleaved area with rhSCGB3A2}/(\text{average of the cleaved area without rhSCGB3A2})\} \times 100$$

It was concluded that the rhSCGB3A2 does inhibit porcine pancreatic sPLA$_2$ and the level of activity is comparable to rhCC10.

Example 6: Comparison of rhSCGB3A2 to Native SCGB3A2 in Human Fluids

Purified rhSCGB3A2 was used to immunize two New Zealand white rabbits, using a standard immunization protocol. The protein was conjugated to KLH, mixed with Freund's adjuvant, and injected into the animals. Both animals produced excellent antibody responses with very high titers. IgG was purified from each set of animal sera using a Pierce Protein A IgG Purification Kit and the purified IgGs were dialyzed into PBS, pH 7.2, aliquoted and stored at −80° C.

The antibodies were qualified by Western blot using tracheal aspirate fluids (TAF) obtained from premature human infants. Samples containing 20 microliters of TAF from 6 infants were run on non-reducing SDS-PAGE and compared to rhSCGB3A2 (5 nanograms). The gel was electro-blotted to PVDF membrane, blocked with 4% non-fat milk, then the highest titer rabbit anti-rhSCGB3A2 IgG (1:5000 dilution) was incubated with the blot, followed by a goat anti-rabbit-HRP conjugate (1:20,000 dilution). The blot was developed using enhanced chemiluminescence (4IPBA-ECL—100 mM Tris/HCl pH 8.8, 1.25 mM luminol, 5.3 mM hydrogen peroxide and 2 mM 4IPBA). Immunoreactive bands appeared in 5/6 of the TAF samples. Two of the samples, (lane 3 and lane 6) contained bands that migrated at the same size as the rhSCGB3A2 homodimer, indicating that the rhSCGB3A2 preparation resembled native human SCGB3A2 in some patients. Heterologous expression of recombinant proteins, especially hydrophobic proteins, for use in animal or human studies often yields misfolded, inactive, immunogenic, or otherwise unusable preparations. Given that the actual N-terminus of native SCGB3A2 is not known and that the pI of rhSCGB3A2 was not as predicted, the observation that at least some human samples contained similar proteins validated our synthetic approach and rhSCGB3A2 preparation. All 5 reactive samples contained high molecular weight species, on the order of 200 kDa and all contained multiple discrete bands in the 8-13 kDa size range, some of which may correspond to monomers, dimers, and alternative isoforms. Two samples (lanes 3 and 7) also contained immunoreactive smears below 3.5 kDa, which likely represent SCGB3A2 degradation products. This is the first time that native SCGB3A2 has been visualized by Western blot. The anti-rhSCGB3A2 antibody used in the Western blot was then used to develop an ELISA for human SCGB3A2.

Example 7: Development of ELISA for rhSCGB3A2

A competitive ELISA was developed using standard methods. In the competitive assay format, the antibody that captures the target is coated onto the wells of the microtiter plate, then an enzyme-conjugated target molecule (labeled target) is used to compete with unconjugated target in the sample for binding to available sites in the well. As the concentration of target in the sample increases, the amount of labeled target that binds to the wells decreases. The rabbit anti-rhSCGB3A2 antibody was coated onto 96 well Maxisorb plates (200 ng/well) then the wells were blocked with 5% sucrose, 2.5% BSA in PBS, then plates are dried and stored at 4° C. A conjugate of horse radish peroxidase (HRP) and rhSCGB3A2 was made (Pierce kit-EZ-Link Maleimide Activated HRP kit, Cat#31494) and was used in the assay diluted 1:130,000. Calibrators (1-500 ng) were made using rhSCGB3A2 and the standard curve was generated as shown in FIG. 6. Native SCGB3A2 was then quantitated in human TAF samples as shown in Table 3.

TABLE 3

Native SCGB3A2 in human TAF

| Lane | Sample | [SCGB3A2] (ng/ml)* |
|---|---|---|
| 1 | Rh-SCGB3A2 (5 ng) | |
| 2 | Infant TAF; Pt. 6 | 774 |
| 3 | Infant TAF; Pt. 7 | 804 |
| 4 | Infant TAF; Pt. 12 | ND |
| 5 | Infant TAF; Pt. 15 | 540 |
| 6 | Infant TAF; Pt 17 | 462 |
| 7 | Infant TAF; Pt. 19 | 395 |
| 8 | Rh-SCGB3A2 (1 ng) | |

SCGB3A2 was also measured in 3 adult human serum samples; returning values of 0, 29, and 32 ng/ml. SCGB3A2 could not be detected in unconcentrated human urine, or urine concentrated 10×. The limit of detection of the assay was 5 ng/ml.

Example 8 a) A method of use of rhCC10 to prevent hospitalization due to a severe respiratory exacerbation in a patient with acute lung injury for a period of up to ten months after administration.
b) A method of use of rhCC10 to prevent a severe respiratory exacerbation in a patient who experiences frequent exacerbations for at least one month after administration.
c) A method of use of rhCC10 to prevent hospitalization due to severe respiratory exacerbations in a patient with a chronic respiratory condition for a period of at least one month after administration.
d) The method of example a-c where in the chronic respiratory condition is COPD.
e) The method of example a-c where in the chronic respiratory condition is asthma.
f) The method of use of rhSCGB3A2 to prevent hospitalization due to a severe respiratory exacerbation in a patient with acute lung injury for a period of up to ten months after administration.
g) The method of use of rhSCGB3A2 to prevent a severe respiratory exacerbation in a patient who experiences frequent exacerbations for at least two months after administration.
h) The method of use of rhSCGB3A2 to prevent hospitalization due to severe respiratory exacerbations in a patient with a chronic respiratory condition for a period of at least one month after administration.
i) The method of use of rhSCGB3A2 to prevent hospitalization due to severe respiratory exacerbations in a patient with a chronic respiratory condition for a period of at least 2 months after administration.
j) The method of examples g-i where in the chronic respiratory condition is pulmonary fibrosis.
k) The method of examples g-i where in the chronic respiratory condition is bronchiectasis. SCGB3A2:
l) A composition of matter for recombinant human SCGB3A2 protein with N-terminus ATA, comprising seq ID 1.
m) A process for synthesizing recombinant human SCGB3A2 using a UBL fusion protein and UBL protease that recognizes the fusion partner and cleaves between the fusion partner and SCGB3A2, to release the intact SCGB3A2 protein according to seq ID 1.
n) A pharmaceutical composition of rhSCGB3A2 that inhibits PLA$_2$ enzymes.
o) A pharmaceutical composition of rhSCGB3A2 that migrates in an isoelectric focusing gel corresponding to isoelectric point at or between 6.3-6.7.
p) A pharmaceutical composition of rhSCGB3A2 comprising a homodimer.
q) A pharmaceutical composition of rhSCGB3A2 comprising a homodimer with pI of 6.7 that inhibits PLA$_2$ enzymes.

While the invention has been described in connection with what is presently considered to be the most practical and preferred embodiments, it is to be understood that the invention is not to be limited to the disclosed embodiments but, on the contrary, is intended to cover various modifications and equivalent arrangements included within the spirit and scope of the appended claims.

ABBREVIATIONS AND DEFINITIONS

CC10: Clara cell 10 kDa protein,
CCSP: Clara cell secretory protein
CC16: Clara cell 16 kDa protein
SCGB1A1: protein encoded by the SCGB1A1 gene, same as CC10, CCSP, CC16, uteroglobin
SCGB3A1: protein encoded by the SCGB3A1 gene, same as HIN-1 and UGRP2
SCGB3A2: protein encoded by the SCGB3A2 gene, same as HIN-2 and UGRP1
HIN-1: high-in-normal protein 1
HIN-2: high-in normal protein 2
UGRP1: uteroglobin gene related protein 1
UGRP2: uteroglobin gene related protein 2
Secretoglobin: Protein from the family of structurally related proteins characterized by four
helical bundle monomers connected by disulfide bonds.
Respiratory secretoglobins: Secretoglobins that are highly expressed and abundant in the respiratory tract, including SCGB1A1, SCGB3A1, and SCGB3A2.

We claim:

1. A method of preventing hospitalization due to a severe respiratory exacerbation in a patient with acute lung injury comprising the steps of:
   (a) administering recombinant human SCGB3A2 (rhSCGB3A2) protein, wherein the rhSCGB3A2 protein consists of the amino acid sequence set forth in SEQ ID NO: 3, to a patient having an acute lung injury, wherein the patient is not re-hospitalized for at least ten months after administration of rhSCGB3A2.

2. A method of preventing hospitalization due to a severe respiratory exacerbation in a patient who experiences frequent respiratory exacerbations comprising the steps of:
   (a) administering recombinant human SCGB3A2 (rhSCGB3A2) protein, wherein the rhSCGB3A2 protein consists of the amino acid sequence set forth in SEQ ID NO: 3, to a patient having frequent respiratory exacerbations, wherein the patient is not re-hospitalized for at least two months after administration of rhSCGB3A2.

3. A method of preventing hospitalization due to a severe respiratory exacerbation in a patient with a chronic respiratory condition comprising the steps of:
   (a) administering recombinant human SCGB3A2 (rhSCGB3A2) protein, wherein the rhSCGB3A2 protein consists of the amino acid sequence set forth in SEQ ID NO: 3, to a patient having a chronic respiratory condition, wherein the patient is not re-hospitalized for at least one month after administration of rhSCGB3A2.

4. The method of claim 1 wherein the severe respiratory exacerbation is caused by pulmonary fibrosis or bronchiectasis.

5. The method of claim 2 wherein the severe respiratory exacerbation is caused by pulmonary fibrosis or bronchiectasis.

* * * * *

SEQUENCE LISTING

<160> NUMBER OF SEQ ID NOS: 12

<210> SEQ ID NO 1
<211> LENGTH: 250
<212> TYPE: DNA
<213> ORGANISM: Homo sapiens

<400> SEQUENCE: 1
cttaagaggt ggtgctaccg ctttcctgat caacaaagtt ccgctgccgg ttgacaaact    60
ggctccgctg ccgctggaca acatcctgcc gttcatggac ccgctgaaac tgctgctgaa   120
aaccctgggt atctctgttg aacacctggt tgaaggtctg cgtaaatgcg ttaacgaact   180
gggtccggaa gcttctgaag ctgttaaaaa actgctggaa gctctgtctc acctggttta   240
gtaaggatcc                                                         250

<210> SEQ ID NO 2
<211> LENGTH: 93
<212> TYPE: PRT
<213> ORGANISM: Homo sapiens

<400> SEQUENCE: 2

Met Lys Leu Val Thr Ile Phe Leu Leu Val Thr Ile Ser Leu Cys Ser
1               5                   10                  15

Tyr Ser Ala Thr Ala Phe Leu Ile Asn Lys Val Pro Leu Pro Val Asp
            20                  25                  30

Lys Leu Ala Pro Leu Pro Leu Asp Asn Ile Leu Pro Phe Met Asp Pro
        35                  40                  45

Leu Lys Leu Leu Leu Lys Thr Leu Gly Ile Ser Val Glu His Leu Val
    50                  55                  60

Glu Gly Leu Arg Lys Cys Val Asn Glu Leu Gly Pro Glu Ala Ser Glu
65                  70                  75                  80

Ala Val Lys Lys Leu Leu Glu Ala Leu Ser His Leu Val
            85                  90

<210> SEQ ID NO 3
<211> LENGTH: 75
<212> TYPE: PRT
<213> ORGANISM: Homo sapiens

<400> SEQUENCE: 3

Ala Thr Ala Phe Leu Ile Asn Lys Val Pro Leu Pro Val Asp Lys Leu
1               5                   10                  15

Ala Pro Leu Pro Leu Asp Asn Ile Leu Pro Phe Met Asp Pro Leu Lys
            20                  25                  30

Leu Leu Leu Lys Thr Leu Gly Ile Ser Val Glu His Leu Val Glu Gly
        35                  40                  45

Leu Arg Lys Cys Val Asn Glu Leu Gly Pro Glu Ala Ser Glu Ala Val
    50                  55                  60

Lys Lys Leu Leu Glu Ala Leu Ser His Leu Val
65                  70                  75

<210> SEQ ID NO 4
<211> LENGTH: 72
<212> TYPE: PRT
<213> ORGANISM: Homo sapiens

<400> SEQUENCE: 4

Phe Leu Ile Asn Lys Val Pro Leu Pro Val Asp Lys Leu Ala Pro Leu
1               5                   10                  15

Pro Leu Asp Asn Ile Leu Pro Phe Met Asp Pro Leu Lys Leu Leu Leu
                20                  25                  30

Lys Thr Leu Gly Ile Ser Val Glu His Leu Val Glu Gly Leu Arg Lys
            35                  40                  45

Cys Val Asn Glu Leu Gly Pro Glu Ala Ser Glu Ala Val Lys Lys Leu
        50                  55                  60

Leu Glu Ala Leu Ser His Leu Val
65                  70

<210> SEQ ID NO 5
<211> LENGTH: 73
<212> TYPE: PRT
<213> ORGANISM: Homo sapiens

<400> SEQUENCE: 5

Ala Phe Leu Ile Asn Lys Val Pro Leu Pro Val Asp Lys Leu Ala Pro
1               5                   10                  15

Leu Pro Leu Asp Asn Ile Leu Pro Phe Met Asp Pro Leu Lys Leu Leu
                20                  25                  30

Leu Lys Thr Leu Gly Ile Ser Val Glu His Leu Val Glu Gly Leu Arg
            35                  40                  45

Lys Cys Val Asn Glu Leu Gly Pro Glu Ala Ser Glu Ala Val Lys Lys
        50                  55                  60

Leu Leu Glu Ala Leu Ser His Leu Val
65                  70

<210> SEQ ID NO 6
<211> LENGTH: 93
<212> TYPE: PRT
<213> ORGANISM: Homo sapiens

<400> SEQUENCE: 6

Met Lys Leu Val Thr Ile Phe Leu Leu Val Thr Ile Ser Leu Cys Ser
1               5                   10                  15

Tyr Ser Ala Thr Ala Phe Leu Ile Asn Lys Val Pro Leu Pro Val Asp
                20                  25                  30

Lys Leu Ala Pro Leu Pro Leu Asp Asn Ile Leu Pro Phe Met Asp Pro
            35                  40                  45

Leu Lys Leu Leu Leu Lys Thr Leu Gly Ile Ser Val Glu His Leu Val
        50                  55                  60

Glu Gly Leu Arg Lys Cys Val Asn Glu Leu Gly Pro Glu Ala Ser Glu
65                  70                  75                  80

Ala Val Lys Lys Leu Leu Glu Ala Leu Ser His Leu Val
                85                  90

<210> SEQ ID NO 7
<211> LENGTH: 74
<212> TYPE: PRT
<213> ORGANISM: Homo sapiens

<400> SEQUENCE: 7

Thr Ala Phe Leu Ile Asn Lys Val Pro Leu Pro Val Asp Lys Leu Ala
1               5                   10                  15

Pro Leu Pro Leu Asp Asn Ile Leu Pro Phe Met Asp Pro Leu Lys Leu

```
                    20                  25                  30

Leu Leu Lys Thr Leu Gly Ile Ser Val Glu His Leu Val Glu Gly Leu
            35                  40                  45

Arg Lys Cys Val Asn Glu Leu Gly Pro Glu Ala Ser Glu Ala Val Lys
        50                  55                  60

Lys Leu Leu Glu Ala Leu Ser His Leu Val
65                  70
```

<210> SEQ ID NO 8
<211> LENGTH: 72
<212> TYPE: PRT
<213> ORGANISM: Homo sapiens

<400> SEQUENCE: 8

```
Phe Leu Ile Asn Lys Val Pro Leu Pro Val Asp Lys Leu Ala Pro Leu
1               5                   10                  15

Pro Leu Asp Asn Ile Leu Pro Phe Met Asp Pro Leu Lys Leu Leu Leu
                20                  25                  30

Lys Thr Leu Gly Ile Ser Val Glu His Leu Val Glu Gly Leu Arg Lys
            35                  40                  45

Cys Val Asn Glu Leu Gly Pro Glu Ala Ser Glu Ala Val Lys Lys Leu
        50                  55                  60

Leu Glu Ala Leu Ser His Leu Val
65                  70
```

<210> SEQ ID NO 9
<211> LENGTH: 58
<212> TYPE: PRT
<213> ORGANISM: Homo sapiens

<400> SEQUENCE: 9

```
Pro Leu Pro Leu Asp Asn Ile Leu Pro Phe Met Asp Pro Leu Lys Leu
1               5                   10                  15

Leu Leu Lys Thr Leu Gly Ile Ser Val Glu His Leu Val Glu Gly Leu
                20                  25                  30

Arg Lys Cys Val Asn Glu Leu Gly Pro Glu Ala Ser Glu Ala Val Lys
            35                  40                  45

Lys Leu Leu Glu Ala Leu Ser His Leu Val
        50                  55
```

<210> SEQ ID NO 10
<211> LENGTH: 73
<212> TYPE: PRT
<213> ORGANISM: Homo sapiens

<400> SEQUENCE: 10

```
Ala Phe Leu Ile Asn Lys Val Pro Leu Pro Val Asp Lys Leu Ala Pro
1               5                   10                  15

Leu Pro Leu Asp Asn Ile Leu Pro Phe Met Asp Pro Leu Lys Leu Leu
                20                  25                  30

Leu Lys Thr Leu Gly Ile Ser Val Glu His Leu Val Glu Gly Leu Arg
            35                  40                  45

Lys Cys Val Asn Glu Leu Gly Pro Glu Ala Ser Glu Ala Val Lys Lys
        50                  55                  60

Leu Leu Glu Ala Leu Ser His Leu Val
65                  70
```

<210> SEQ ID NO 11

```
<211> LENGTH: 70
<212> TYPE: PRT
<213> ORGANISM: Homo sapiens

<400> SEQUENCE: 11

Glu Ile Cys Pro Ser Phe Gln Arg Val Ile Glu Thr Leu Leu Met Asp
1               5                   10                  15

Thr Pro Ser Ser Tyr Glu Ala Ala Met Glu Leu Phe Ser Pro Asp Gln
            20                  25                  30

Asp Met Arg Glu Ala Gly Ala Gln Leu Lys Lys Leu Val Asp Thr Leu
        35                  40                  45

Pro Gln Lys Pro Arg Glu Ser Ile Ile Lys Leu Met Glu Lys Ile Ala
    50                  55                  60

Gln Ser Ser Leu Cys Asn
65              70

<210> SEQ ID NO 12
<211> LENGTH: 86
<212> TYPE: PRT
<213> ORGANISM: Homo sapiens

<400> SEQUENCE: 12

Ala Ala Phe Leu Val Gly Ser Ala Lys Pro Val Ala Gln Pro Val Ala
1               5                   10                  15

Ala Leu Glu Ser Ala Ala Glu Ala Gly Ala Gly Thr Leu Ala Asn Pro
            20                  25                  30

Leu Gly Thr Leu Asn Pro Leu Lys Leu Leu Leu Ser Ser Leu Gly Ile
        35                  40                  45

Pro Val Asn His Leu Ile Glu Gly Ser Gln Lys Cys Val Ala Glu Leu
    50                  55                  60

Gly Pro Gln Ala Val Gly Ala Val Lys Ala Leu Lys Ala Leu Leu Gly
65                  70                  75                  80

Ala Leu Thr Val Phe Gly
                85
```